US00PP11477P

United States Patent [19]

Waldner et al.

[11] Patent Number: Plant 11,477

[45] Date of Patent: Aug. 8, 2000

[54] NECTARINE TREE NAMED 'AUGUST FIRE'

[76] Inventors: Norman Waldner; Michael Waldner, both of 8936 Ave. 396, Dinuba, Calif. 93618

[21] Appl. No.: 09/200,549

[22] Filed: Nov. 27, 1998

[51] Int. Cl.[7] ..... A01H 5/00

[52] U.S. Cl. ..... Plt./190

[58] Field of Search ..... Plt./190, 188, 187

[56] References Cited

U.S. PATENT DOCUMENTS

P.P. 6,363 11/1988 Bradford et al. ..... Plt./190

P.P. 8,002 10/1992 Bradford et al. ..... Plt./190

*Primary Examiner*—Howard J. Locker

[57] ABSTRACT

The present invention relates to a nectarine tree, *Prunus persica*, and more particularly to a new and distinct variety broadly characterized by a large size, vigorous, self-fertile, productive and regular bearing tree. The fruit matures under the ecological conditions described approximately the third week in August, with first picking on Aug. 17, 1988. The fruit is uniformly large in size, acidic in flavor, globose in shape, clingstone in type, very firm and crispy in texture, and nearly full red in skin color. The vriety was discovered as a mutation of one of the three main scaffolds of an 'August Red' (U.S. Plant Pat. No. 6, 363) nectarine tree in a commercial orchard.

1 Drawing Sheet

BACKGROUND OF THE VARIETY

We, the discoverers, are commercial stone fruit growers at Waldner Farms near Dinuba, Calf. in Tulare County (San Joaquin Valley). In 1988 we planted a 10 acre orchard of 'August Red' (U.S. Plant Pat. No. 6,363) nectarines in a cultivated area of our property. In 1993 we discovered a tree in that orchard having an apparent mutation on one of its three main scaffolds. All of the fruit on this scaffold ripened about 1 week earlier than the fruit on the other two scaffolds. The fruit on the mutated limb was virtually one hundred percent red, while the fuit on the other two scaffolds reached only about fifty percent red at full maturity. Subsequent to the discovery of this mutated scaffold, we asexually reproduced it by budding and grafting on Nemaguard rootstock. Also, we grafted scions from the mutated scaffold and 'August Red', side by side, onto a Nemaguard rootstock to substantiate its uniqueness from the 'August Red'. The reproduction of plant and fruit characteristics of this newly discovered nectarine variety proved true to the original mutated scaffold in all respects. Also, one of the inventors of the 'August Red', Lowell Bradford, inspected the original mutated limb and the multiplied trees and acknowledged its uniqueness from the 'August Red'. In accordoance with our observations for 5 years, we have demonstrated that the present discovery relates to a new and distinct variety of nectarine tree, which has been denominated varietally as 'AUGUST FIRE'.

The present variety is most similar to the 'August Red' nectarine tree by having a similar tree in size, vigor, and productivity and by producing large clingstone nectarines that are acidic in flavor, very firm in texture, and that ripen in August, but is distinguished therefrom and an improvement thereon by producing fruit that ripens about 7 days earlier and that has a much higher percent of red skin color over the surface area.

DRAWING

The accompanying photograph exhibits four whole fruits positioned to display the characteristics of the skin color and form, one fruit divided transversely to the suture plane to reveal the flesh and stone, and typical leaves.

POMOLOGICAL CHARACTERISTICS

Referring now more specifically to the pomological characteristics of this new and distinct variety of nectarine tree, the following has been observed under the ecological conditions prevailing near Dinuba, Tulare County (San Joaquin Valley), Calif., and was developed at the state of hard shipping ripe on Aug. 17, 1998. All major color code designations are by reference to the Inter-Society Color council, National Bureau of Standards. Common color names are also used occasionally.

TREE

Size: Large, reaching a height of 13' [3.96 meters] by the 6th year of commercial farming, including typical dormant pruning.

Vigor: Vigorous, responding typically to irrigation and fertilization.

Growth: Upright and dense.

Form: Vase formed.

Hardiness: Hardy with respect to typical central California winters.

Production: Productive, thinning necessary.

Fertility: Self-fertile.

Bearing: Regular bearer, with no alternate bearing observed.

Trunk and main scaffolds:

*Size.*—Medium, the main scaffold reaching a diameter of 5" [127 mm.] after 9 years of growth.

*Textue.*—Rough.

*Bark color.*—Grayish yellowish brown [80. gy.yBr].

*Lenticels.*—Numerous. Color: Moderate orange yellow [71. m.OY]. Average size 3/16" to 4/16" [4.8–11.1 mm.].

Branches:

*Size.*—Medium, typical of the species.

*Texture.*—Smooth on 1st year wood, increasing roughness with age.

*Color.*—1st Year Wood Topside: Light grayish red [18. l.gy.R]. 1st Year Wood Underside: Brilliant yellow green [116. brill.YG]. Older Wood: Moderate Yellowish brown [77. m.yBr].

*Lenticels.*—Numerous, small. Color: Light yellowish brown [76. l.yBr]. Size: 1/16" to 5/16" [1.6 - 7.9 mm.].

Leaves:
*Size.*—Large. Average Length: 6 ⅛" [155.6 mm.]. Average Width: 1 ⅝" [41.3 mm.].
*Thickness.*—Medium.
*Form.*—Elliptical.
*Apex.*—Acutely pointed to acuminate.
*Base.*—Acute.
*Surface.*—Smooth.
*Color.*—Dorsal Surface: Moderate olive green [125. m.OlG]. Ventral Surface: Moderate yellow green [120. m.YG].
*Margin.*—Finely serrate.
*Venation.*—Pinnately net veined.
*Petiole.*—Average Length: ⅜" [9.5 mm.]. Average Thickness: 1/16" [1.6 mm.]. Color: Light Yellow green [119. l.YG].
*Stipules.*—2 per leaf bud, up to 6 at the growing tip. Average Length: ¼" [6.4 mm.].
*Glands.*—Numbers: 2 to 4 per leaf. Position: Alternately Positioned on petiole and base of blade. Size: Medium. Form: Reniform. Color: Moderate reddish brown [43. m.rBr].

Flower buds:
*Hardiness.*—Hardy with respect to central California winters.
*Diameter.*—Typically ⅜" [9.5 mm.] 1 week before bloom.
*Length.*—Typically ⅝" [15.9 mm.] 1 week before bloom.
*Form.*—Free.
*Surface.*—Pubescent.

Flowers:
*Blooming period.*—Medium as compared with other varieties.
*Onset of bloom.*—One percent on Feb. 24, 1998.
*Type.*—Non-showy.
*Average diameter.*—1 ⅜" [34.9 mm.].
*Color.*—Moderate purplish red [258. m.pR].

FRUIT

Maturity when described: Hard shipping ripe, Aug. 21, 1998.
Date of first picking: Aug. 17, 1998.
Date of last picking: Aug. 31, 1998.
Size: Uniform, large.
*Average diameter axially.*—2 ¾" [69.9 mm.].
*Average transversely in suture plane.*—2 ¾" [69.9 mm.].
*Typical weight.*—7.46 ounces [211 grams].
Form: Globose, uniform, symmetrical.
*Longitudinal section form.*—Round.
*Transverse section through diameter.*—Round.
Suture: An inconspicuous line near the base becoming a shallow groove toward the apex with a slight depression beyond the pistil point.
Ventral surface: Rounded, lipped stronger toward the apex.
Lips: Unequal.
Cavity: Rounded, elongated in the suture plane, suture showing on one side, stem markings typical.
*Depth.*—½" [12.7 mm.].
*Breadth.*—¾" [19.1 mm.].
Base: Rounded to slightly truncate.
Apex: Rounded.
Pistil point: Short, apical, most indented within the suture with a few protruding slightly.

Stem: Medium.
*Average length.*—⅜" [9.5 mm.].
*Average width.*—3/16" [4.8 mm.].

Skin:
*Thickness.*—Medium.
*Texture.*—Medium.
*Tenacity.*—Tenacious to flesh.
*Tendency to crack.*—None observed.
*Color.*—Deep red [13. deep R] over a deep reddish orange [36. deep rO] background, with an occasional brilliant yellow [83. brill.Y] sun protected area.

Flesh:
*Color.*—Brilliant yellow [83. brill.Y] with some minor vivid red [11. v.R] streaking near the stone.
*Surface of pit cavity.*—vivid red [11. v.R] fibers breaking when twisted away from the stone.
*Amygdalin.*—Abundant.
*Juice.*—Moderate, rich.
*Texture.*—Very firm, crisp.
*Fibers.*—Abundant, fine.
*Ripens.*—Slightly earlier at the apex and along the cheeks.
*Flavor.*—Acidic with a nice blend of sugar, averaging 13 brix.
*Aroma.*—Very slight.
*Eating quality.*—Very good.

STONE

Type: Clingstone.
Form: oval.
Base: Straight.
Apex: Acute.
Hilum: Narrow.
Sides: Equal.
Surface: Irregularly furrowed toward the apex, pitted near the base.
Ridges: Jagged toward the base.
Color: Deep brown [56. deep Br] when dry.
Pit wall: ¼" [6.4 mm.] thick.
Tendency to split: None observed.
Kernel:
*Form.*—Oval.
*Taste.*—Slightly bitter.
*Viable.*—Yes.
*Average width.*—9/16" [14.3 mm.].
*Average length.*—13/16" [20.6 mm.].
*Skin color.*—Brilliant yellow [83. brill.Y] with strong yellowish brown [74. s.yBr] veins when first removed from stone.
*Pellicle color.*—Grayish brown [61. gy.Br].
*Amygdalin.*—Scant.

USE

Market: Fresh and long distance shipping.
Keeping quality: Fruit quality observed to remain in good condition in excess of 21 days in cold room at 36° F. [2° C.].
Resistance to insects: No unusual susceptibilities noted.
Resistance to diseases: A susceptibility to potassium deficiency observed, no other unusual susceptibilities noted.

Although the new variety of nectarine tree possesses the described characteristics under the ecological conditions at Dinuba, Calif., in the central part of the San Joaquin Valley, it is to be expected that variations in these characteristics may occur when farmed in areas with different climatic condition, different soil types, and/or varying cultural practices.

We claim:

1. A new and distinct variety of nectarine tree, substantially as illustrated and described, that is most similar to the 'August Red' (U.S. Plant Pat. No. 6,363) nectarine tree by having a similar tree in size, vigor, and productivity and by producing large clingstone nectarines that are acidic in flavor, very firm in texture, and that ripen in August, but is distinguished therefrom and an improvement thereon by producing fruit that ripens about 7 days earlier and that has a much higher percent of red skin color over the surface area.

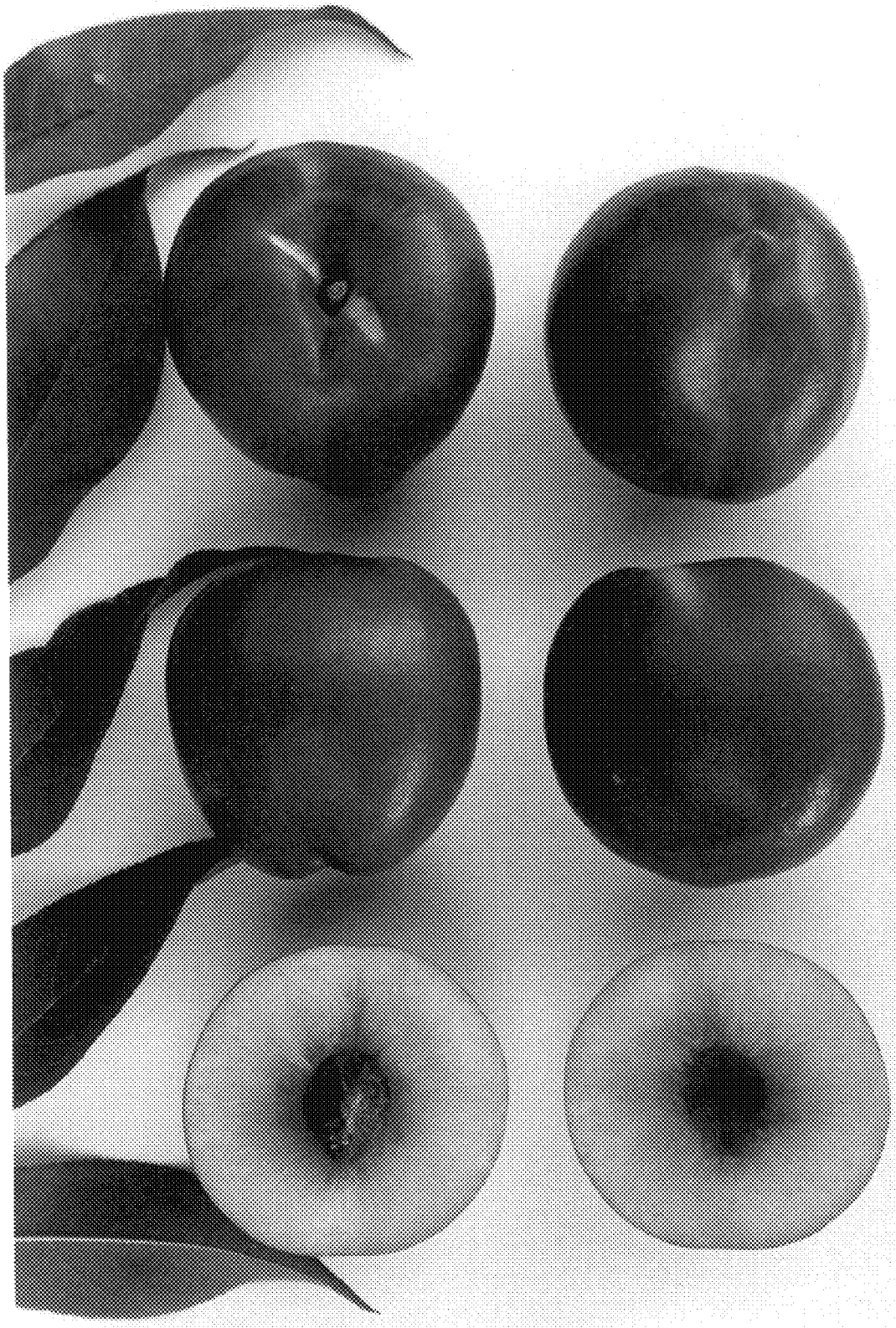

* * * * *